US012201509B2

(12) United States Patent
Tranquillo et al.

(10) Patent No.: US 12,201,509 B2
(45) Date of Patent: *Jan. 21, 2025

(54) DECELLULARIZED BIOLOGICALLY-ENGINEERED TUBULAR GRAFTS

(71) Applicant: Regents of the University of Minnesota, Minneapolis, MN (US)

(72) Inventors: Robert Tranquillo, Arden Hills, MN (US); Zeeshan Syedain, Minneapolis, MN (US); Lee Meier, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/117,930

(22) Filed: Mar. 6, 2023

(65) Prior Publication Data
US 2023/0277293 A1 Sep. 7, 2023

Related U.S. Application Data

(60) Continuation of application No. 17/139,575, filed on Dec. 31, 2020, now Pat. No. 11,596,512, which is a
(Continued)

(51) Int. Cl.
*A61F 2/04* (2013.01)
*A61F 2/06* (2013.01)
(Continued)

(52) U.S. Cl.
CPC .............. *A61F 2/06* (2013.01); *A61F 2/04* (2013.01); *A61F 2/2412* (2013.01);
(Continued)

(58) Field of Classification Search
CPC .. A61F 2/04; A61F 2/06; A61F 2/2412; A61F 2/2415; A61L 27/507;
(Continued)

(56) References Cited

U.S. PATENT DOCUMENTS

| 6,666,886 B1 | 12/2003 | Tranquillo et al. |
| 10,105,208 B2 | 10/2018 | Tranquillo et al. |

(Continued)

FOREIGN PATENT DOCUMENTS

| WO | WO 2007/025233 | 3/2007 |
| WO | WO 2010/120539 | 10/2010 |

(Continued)

OTHER PUBLICATIONS

Baptista et al., "Whole organ decellularization—a tool for bioscaffold fabrication and organ bioengineering," Annu. Int. Conf. Proc. IEEE Eng. Med. Biol. Soc., 2009, 2009:6526-6529.
(Continued)

*Primary Examiner* — Dinah Baria
(74) *Attorney, Agent, or Firm* — Fish & Richardson P.C.

(57) ABSTRACT

This disclosure describes decellularized, biologically-engineered tubular grafts and methods of making and using such decellularized, biologically-engineered tubular grafts.

11 Claims, 3 Drawing Sheets

Related U.S. Application Data continuation of application No. 16/045,220, filed on Jul. 25, 2018, now Pat. No. 10,893,928, which is a continuation of application No. 14/633,268, filed on Feb. 27, 2015, now Pat. No. 10,105,208, which is a division of application No. 13/771,676, filed on Feb. 20, 2013, now Pat. No. 10,111,740.

(60) Provisional application No. 61/691,394, filed on Aug. 21, 2012.

(51) Int. Cl.
*A61F 2/24* (2006.01)
*A61L 27/36* (2006.01)
*A61L 27/50* (2006.01)
*B29D 23/00* (2006.01)

(52) U.S. Cl.
CPC ............ *A61F 2/2415* (2013.01); *A61L 27/36* (2013.01); *A61L 27/3604* (2013.01); *A61L 27/3633* (2013.01); *A61L 27/3695* (2013.01); *A61L 27/507* (2013.01); *B29D 23/00* (2013.01); *A61F 2/062* (2013.01); *A61L 2430/40* (2013.01)

(58) Field of Classification Search
CPC .. A61L 27/363; A61L 27/3604; A61L 27/225; A61L 2430/40
See application file for complete search history.

(56) References Cited

U.S. PATENT DOCUMENTS

| | | |
|---|---|---|
| 10,111,740 B2 | 10/2018 | Tranquillo et al. |
| 10,893,928 B2 | 1/2021 | Tranquillo et al. |
| 2004/0115176 A1 | 6/2004 | Swartz et al. |
| 2006/0153815 A1 | 7/2006 | Seyda et al. |
| 2006/0217802 A1 | 9/2006 | Ruiz et al. |
| 2007/0128171 A1* | 6/2007 | Tranquillo ............ A61L 27/507 435/325 |
| 2011/0008397 A1 | 1/2011 | Cohen |
| 2014/0058496 A1 | 2/2014 | Tranquillo et al. |
| 2015/0164631 A1 | 6/2015 | Tranquillo et al. |
| 2018/0325650 A1 | 7/2018 | Tranquillo et al. |
| 2021/0369437 A1 | 12/2021 | Tranquillo et al. |

FOREIGN PATENT DOCUMENTS

| | | |
|---|---|---|
| WO | WO 2013/090878 | 6/2013 |
| WO | WO 2018/102826 | 6/2018 |
| WO | WO 2019/006430 | 1/2019 |

OTHER PUBLICATIONS

Crapo et al. "An overview of tissue and whole organ decellularization processes," Biomaterials, Apr. 2011, 32(12):3233-3243.
Grenier et al., "Tissue Reorganization in Response to Mechanical Load Increases Functionality," Tissue Engineering, Feb. 2005, 11(1-2):90-100.
Guillemette et al., "Surface topography induces 3D self-orientation of cells and extracellular matrix resulting in improved tissue function," Integrative Biology, 2009(1):196-204.
Konig et al., "Mechanical properties of completely autologous human tissue engineered blood vessels compared to human saphenous vein and mammary artery," Biomaterials, Mar. 2009, 30(8):1542-1550.
L'Heureux et al., "A completely biological tissue-engineered human blood vessel," FASEB J., Jan. 1998, 12(1):47-56.
McAllister et al., "Effectiveness of haemodialysis access with an autologous tissue-engineered vascular graft: a multicentre cohort study," Lancet, Apr. 2009, 373 (9673): 1440-1446.
Ott et al., "Perfusion-decellularized matrix: using nature's platform to engineer a bioartificial heart," Nat Med., Feb. 2008, 14(2):213-221.
Suggs et al., "Preparation and characterization of poly(propylene fumarate-co-ethylene glycol) hydrogels," J. Biomater. Sci. Polym. Ed., Jan. 1998, 9(7):653-966.
Syedain et al., "Implantable arterial grafts from human fibroblasts and fibrin using a multi-graft pulsed flow-stretch bioreactor with noninvasive strength monitoring," Biomaterials, Jan. 2011, 32(3):714-722.
Syedain et al., "Tissue engineering of accellular vascular grafts capable of somatic growth in young lambs," Nature Communications., Sep. 2016, 7:12951, 9 pages.
White et al., "A Stentless Trileaflet Valve From a Sheet of Decellularized Porcine Small Intestinal Submucosa," Ann. Thorac. Surg., Aug. 2005, (80):704-707.

\* cited by examiner

Step 1: Engineer a tissue tube with circumferential fiber alignment. Remove cells by detergent treatment, creating a decellularized engineered tissue tube Step 2: Anchor the tube at multiple points with suture, metallic, or polymer posts Step 3: With flow, the tube drops inward creating leaflets with functional valve action

DECELLULARIZED BIOLOGICALLY-ENGINEERED TUBULAR GRAFTS

CROSS REFERENCE TO RELATED APPLICATIONS

This application is a Continuation of U.S. application Ser. No. 17/139,575 filed on Dec. 31, 2020, which is a Continuation of U.S. application Ser. No. 16/045,220 filed Jul. 25, 2018 (now U.S. Pat. No. 10,893,928), which is a Continuation of U.S. application Ser. No. 14/633,268 filed Feb. 27, 2015 (now U.S. Pat. No. 10,105,208), which is a Divisional of U.S. application Ser. No. 13/771,676 filed Feb. 20, 2013 (now U.S. Pat. No. 10,111,740), which claims the benefit of priority under 35 U.S.C. § 119(e) to U.S. Application No. 61/691,394 filed Aug. 21, 2012.

FEDERALLY SPONSORED RESEARCH OR DEVELOPMENT

This invention was made with government support under HL071538, HL107572, and HL083880 awarded by the National Institutes of Health. The government has certain rights in the invention.

TECHNICAL FIELD

This disclosure generally relates to decellularized tubular grafts and methods of making and using such decellularized tubular grafts.

BACKGROUND

Cardiovascular disease is the leading cause of mortality in the world: approximately one million surgical procedures are performed annually in the US alone. Vascular grafts made from synthetic polyesters have shown success in replacement of large diameter vessels such as the thoracic and abdominal aortas, aortic arch vessels, as well as the iliac and femoral arteries. However, they have generally proven inadequate as small-diameter (<6 mm) arterial grafts. This is primarily a result of acute graft thrombogenicity, anastomotic intimal hyperplasia, aneurysm formation and infection. Autologous arteries and veins remain the standard of care. However, a significant fraction of patients do not have a suitable vessel that can be harvested as a replacement and donor site morbidity occurs. Therefore, tissue engineering provides a viable alternative to create arterial grafts that can maintain vascular function comparable to native vessels.

SUMMARY

This disclosure describes decellularized tubular grafts and methods of making and using such decellularized tubular grafts.

In one aspect, a decellularized, biologically-engineered tubular graft is provided. Such a biologically-engineered tubular graft includes cell-produced extracellular matrix, wherein fibers within the biologically-engineered tubular graft are aligned circumferentially. Such a decellularized, biologically-engineered tubular graft exhibits greater tensile stiffness in the circumferential direction than in the longitudinal direction and exhibits a burst pressure that statistically significantly exceeds a physiological pressure. In another aspect, a biologically-engineered tubular valve is provided that includes a decellularized, biologically-engineered tubular graft.

The cell-produced extracellular matrix can originate from a composition that includes matrix-producing cells, fibrinogen or a fibrinogen-like material, and thrombin. In some embodiments, the matrix-producing cells are fibroblasts such as human dermal fibroblasts.

In some embodiments, the tubular graft exhibits a burst pressure of at least 2500 mm Hg, at least 3000 mm Hg, at least 3500 mm Hg, or at least 4000 mm Hg. In some embodiments, the tubular graft has an average diameter of about 0.5 mm to about 6 mm, about 5 mm to about 12 mm, about 10 mm to about 20 mm, or about 18 mm to about 24 mm. Representative tubular grafts include, without limitation, a vascular graft (e.g., an arterial graft or a venous graft), a urethra graft, a fallopian tube graft, a Vas deferens graft, or a Eustachian tube graft.

In another aspect, a method of making the decellularized, biologically-engineered tubular graft described herein is provided. Such a method typically includes combining fibrinogen or fibrinogen-like material, thrombin, and matrix-producing cells to produce a cell-seeded fibrin gel; molding the cell-seeded fibrin gel into the shape of a hollow tube; manipulating, mechanically, the tube in the presence of culture medium to produce a biologically-engineered tubular graft; and decellularizing the biologically-engineered tubular graft. In some embodiments, such a method further can include anchoring one end of the decellularized, biologically-engineered tubular graft at two positions, three positions, or four positions to shape the decellularized, biologically-engineered tubular graft into a bi-, tri- or quad-leaflet valve, respectively. In still another aspect, a biologically-engineered valve made by such a method is provided.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
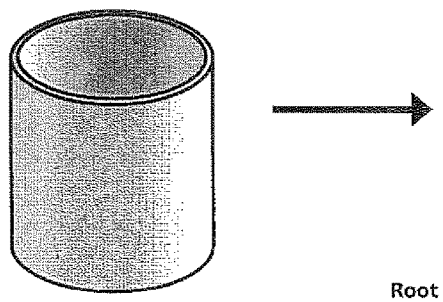
FIG. 1 is a schematic showing a representative method of using a decellularized, biologically-engineered tubular graft to make a biologically-engineered valve.
Figure 1:
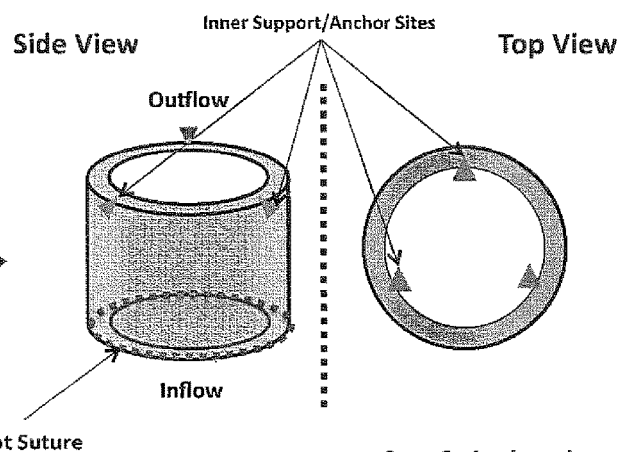
Figure 1:
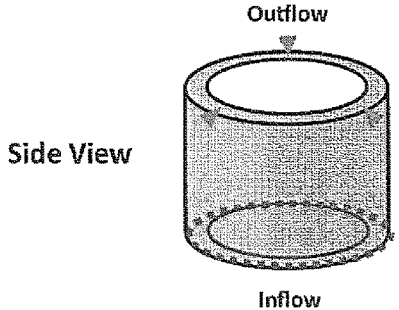
Figure 1:
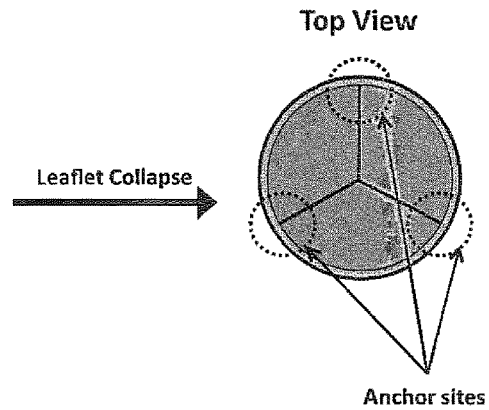

This disclosure describes a method of making the decellularized, biologically-engineered tubular graft and also describes the subsequently produced decellularized, biologically-engineered tubular graft. Initially, fibrinogen or fibrinogen-like material, thrombin, and matrix-producing cells are combined, and the resulting cell-seeded gel composition is molded into the shape of a hollow tube. The fibrin-based gel is remodeled into an extracellular matrix by the matrix-producing cells, which retains the tubular shape of the original mold.

Fibrinogen is a well known soluble glycoprotein naturally found in blood, and is converted to fibrin by the action of thrombin, a serine protease, during blood coagulation. As used herein, fibrinogen-like material refers to proteins, natural or synthetic, that have similar characteristics to those of fibrinogen and, which, as described herein, can be converted into a fibrin-like material and, eventually, into an extracellular matrix material. One example of a fibrinogen-like material is PEGylated-fibrinogen (see, for example, Suggs et al., 1998, *J. Biomater. Sci. Polym. Ed.,* 9:653-66).

As used herein, "matrix-producing cells" are those cells that have the capability of converting fibrinogen or a fibrinogen-like material, in the presence of thrombin, into extracellular matrix. As described herein, fibroblast cells are very efficient at producing extracellular matrix material as are smooth muscle cells. Fibroblasts are well known and can be human fibroblasts, primate fibroblasts, rodent fibroblasts, or any other type of mammalian fibroblasts. Fibroblasts can be obtained from, for example, any number of different anatomical tissues (e.g., dermis, lung, connective tissue, kidney, etc.), commercial sources (e.g., Millipore, Cell Applications, StemGent, etc.), and/or biological depositories (e.g., American Type Culture Collection (ATCC)). The same is true for smooth muscle cells. The matrix-producing cells can be combined with the fibrinogen or fibrinogen-like material, and the thrombin and then molded, or the matrix-producing cells can be seeded into a composition that includes fibrinogen or fibrinogen-like material and thrombin and that has been molded into a tubular shape.

While matrix-producing cells at any passage beyond three passages (e.g., four, five, six, seven, eight, nine, or ten passages) can be used in combination with the fibrinogen or fibrinogen-like material, it is preferred that the matrix-producing cells that are used have been grown for between three passages and seven passages. For example, fibroblasts can be grown for between three passages and six passages, for between four passages and six passages, for between four passages and seven passages, or for between five passages and seven passages. In addition, the number of matrix-producing cells used initially in a tubular graft as described herein can be, for example, from about $10^2$ cells to about $10^{12}$ cells (e.g., about $10^3$ cells to about $10^{10}$ cells, about $10^4$ cells to about $10^9$ cells, $10^5$ cells to about $10^8$ cells, or about $10^6$ cells to about $10^7$ cells).

Hydrogels are well known in the art and generally refer to hydrophilic polymeric chains that can contain natural or synthetic polymers. One or more hydrogels optionally can be included in the composition. Any number of suitable hydrogels can be used, if desired, to support and mold the cell-seeded fibrin gel (e.g., comprising fibrinogen or fibrinogen-like material and the matrix-producing cells) as necessary. Representative hydrogels include, for example, agarose, methylcellulose, hyaluronan, and combinations thereof. If present, the amount of hydrogel used in a composition described herein can range from about 10% to about 80% (e.g., about 20% to about 70%, about 30% to about 60%, about 40% to about 50%, or about 50%). The presence of and the actual amount of one or more hydrogels will depend upon the desired features of the cell-seeded fibrin gel or the subsequently produced biologically-engineered tubular graft (e.g., softness or hardness, flexibility, absorbency).

The cell-seeded gel can be molded around, for example, a mandrel, in order to obtain a hollow tube. Mandrels of different sizes can be used depending upon the desired size of the hollow tube. For example, a tubular graft as described herein can have a diameter of about 0.5 mm up to a diameter of about 24 mm (e.g., about 1 mm, about 2 mm, about 5 mm, about 10 mm, about 15 mm, about 20 mm, about 21 mm, about 22 mm, about 23 mm, or about 24 mm in diameter; about 0.5 mm to about 6 mm, about 5 mm to about 12 mm, about 10 mm to about 18 mm, about 15 mm to about 21 mm, about 20 mm to about 24 mm, or about 18 mm to about 24 mm in diameter). In some embodiments, the diameter of the tubular graft can be an appropriate size for use as a vascular graft (e.g., an arterial or venous graft, or arterio-venous fistula). For example and without limitation, the diameter of the tubular graft can be an appropriate size for use as a graft for a urethra, a fallopian tube, a Vas deferens, or a Eustachian tube. In addition, the larger diameter tubular grafts can be used to encircle or ensheath a structure such as, without limitation, a heart valve construct. The length of the tubular graft will be any length that is appropriate or necessary to graft. For example, a tubular graft as described herein can be from about 3.0 mm up to about 20 cm in length (e.g., about 3.0 mm to about 10.0 mm, about 5.0 mm to about 20.0 mm, about 25.0 mm to about 5.0 cm, about 50.0 mm to about 10 cm, about 10 cm to about 15 cm, about 10 cm to about 20 cm, about 15 cm to about 20 cm in length).

This combination of materials, over time, is converted by the cells into an extracellular matrix (referred to herein as a "cell-produced extracellular matrix"), typically in a controlled laboratory setting. While the tubular graft is undergoing this transformation from the cell-seeded gel into the cell-produced extracellular matrix, the tubular graft can be mechanically manipulated (or "conditioned") in any number of fashions. Mechanical manipulations include, for example, static culture on the mandrel, which, for a non-adhesive mandrel, leads to circumferential alignment as the cells compact the gel, causing the axial length to shorten, and circumferential stretching or distension while providing for axial shortening to maintain the circumferential alignment. Generally, such stretching or distortion is cyclic or periodic. See, for example, Syedain et al., 2011, *Biomaterials,* 32:714-22. Simply by way of example, mechanical manipulations of the cell-seeded gel as it is remodeled into a cell-produced extracellular matrix can be performed using flow-stretch or pulsed flow-stretch methods in any number of bioreactors.

Such mechanical manipulation typically is done in the presence of culture medium in order to maintain cell viability during the conversion process. The culture medium is the same medium usually used to culture cells such as fibroblasts, and includes components such as, without limitation, serum, amino acids, salts (e.g., calcium chloride, potassium chloride, magnesium sulfate, sodium chloride, and/or monosodium phosphate), glucose, and vitamins (e.g., folic acid, nicotinamide, riboflavin, and/or $B_{12}$).

The biologically-engineered tubular graft then can be decellularized. Decellularization can take place using any number of different methods. See, for example, WO 2007/025233, WO 2010/120539, Ott et al. (2008, *Nat. Med.,* 14:213-21), Baptista et al. (2009, *Conf Proc. IEEE Eng. Med. Biol. Soc.,* 2009:6526-9) or Crapo et al. (2011, *Biomaterials,* 32:3233-43).

The resulting decellularized, biologically-engineered tubular graft exhibits a number of novel features. For example, the fibers are aligned circumferentially around the tubular graft, which results in a decellularized, biologically-engineered tubular graft that exhibits greater tensile stiffness in the circumferential direction than in the longitudinal direction. In addition, the decellularized, biologically-engineered tubular graft described herein exhibits a burst pressure that exceeds, and, in many cases, statistically significantly exceeds, the pressure to which vasculature is normally or typically exposed (i.e., physiological pressure). For example, a decellularized, biologically-engineered tubular graft described herein can withstand a pressure of at least 2000 mm Hg, at least 2500 mm Hg, at least 3000 mm Hg, at least 3500 mm Hg, at least 4000 mm Hg, or greater than 4000 mm Hg, without bursting. In other words, a decellularized, biologically-engineered tubular graft described herein can exhibit a burst pressure of at least 2000 mm Hg, at least 2500 mm Hg, at least 3000 mm Hg, at least 3500 mm Hg, at least 4000 mm Hg, or greater than 4000 mm Hg. Moreover, the cell-produced extracellular matrix is conducive to recellularization (i.e., cells, including endothelial cells populating the luminal surface and tissue cells penetrating and repopulating the interior cavity) both in culture in the laboratory and endogenously following implantation or engraftment.

As indicated herein, a decellularized, biologically-engineered tubular graft can be implanted or engrafted directly following decellularization. Alternatively, a decellularized, biologically-engineered tubular graft can be used to form a tissue-engineered valve before being implanted or engrafted. For example, one end of a decellularized, biologically-engineered tubular graft as described herein can be anchored at two points (for a bi-leaflet valve), three points (for a tri-leaflet valve) or four points (for a quad-leaflet valve) using a suture, an adhesive, or other suitable bonding method.

Figure 2:
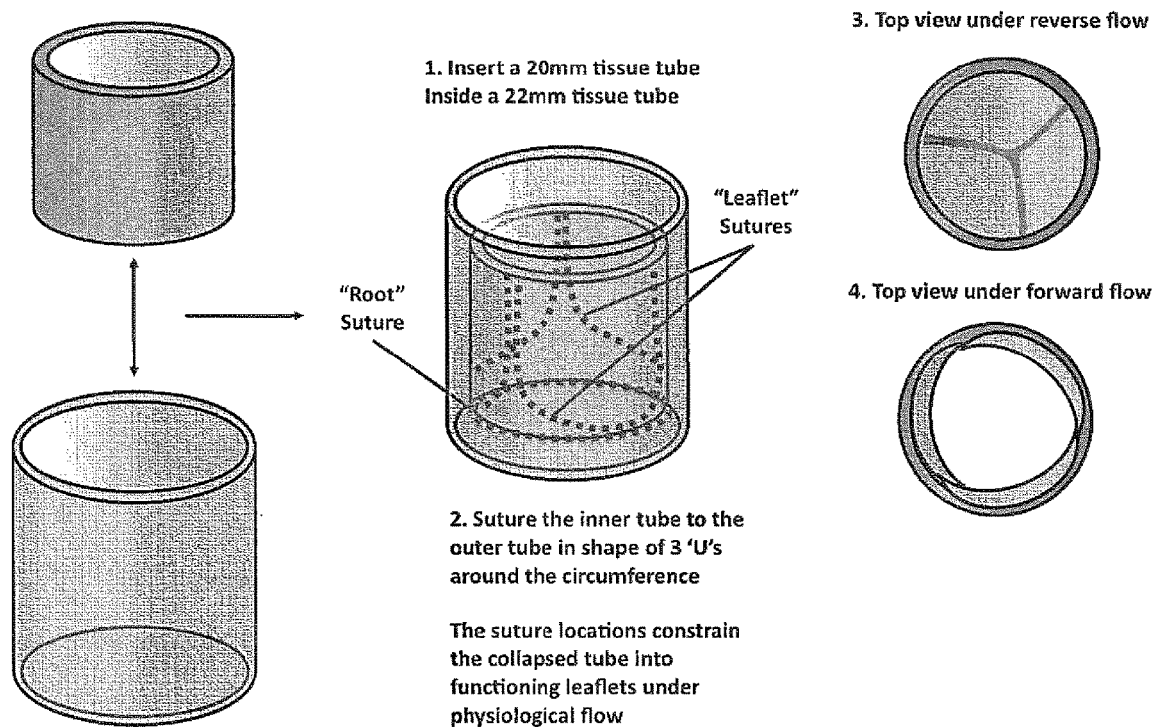
FIG. 2 is a schematic showing a representative method of using a decellularized, biologically-engineered tubular graft to make a biologically-engineered valve. The anchor points in FIG. 2 are created by suturing one tube within another.

The schematic shown in FIG. 1 shows a structure in which three anchoring points are created. This leads to the formation of a structure, which, under fluid back-pressure, causes the tube to collapse and create a valvular action that is very similar to a tri-leaflet valve. Alternatively, FIG. 2 is a schematic showing an embodiment in which one tube is sutured to a tube placed over the first tube. As shown in FIG. 2, suture lines are created that define three 'U' shapes around the circumference of the tube. This leads to the formation of a structure as described above that, under fluid back-pressure, causes the inner tube to collapse and create a valvular action that is very similar to a tri-leaflet valve.

Figure 3:
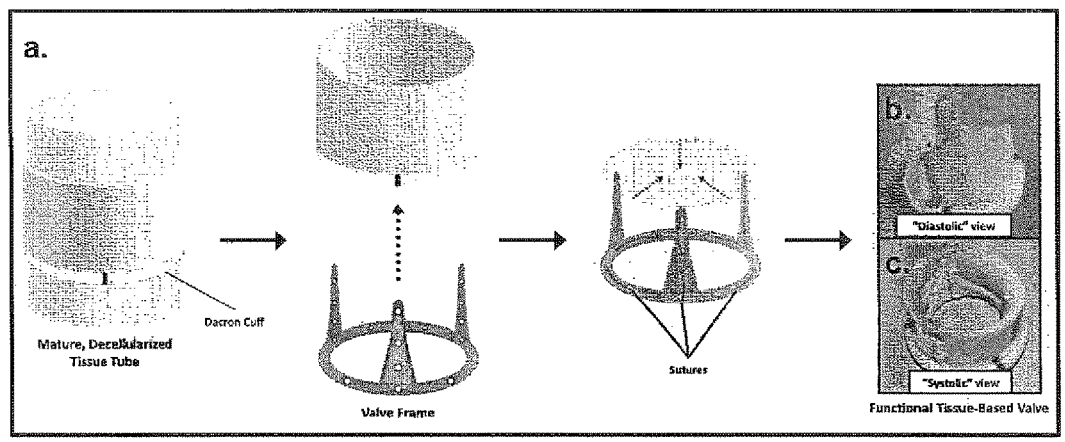
FIG. 3 is a schematic, including photographs, showing a representative method of using a decellularized biologically-engineered tubular graft to make a biologically-engineered valve. A frame in FIG. 3 provides the anchor points.
Figure 3:
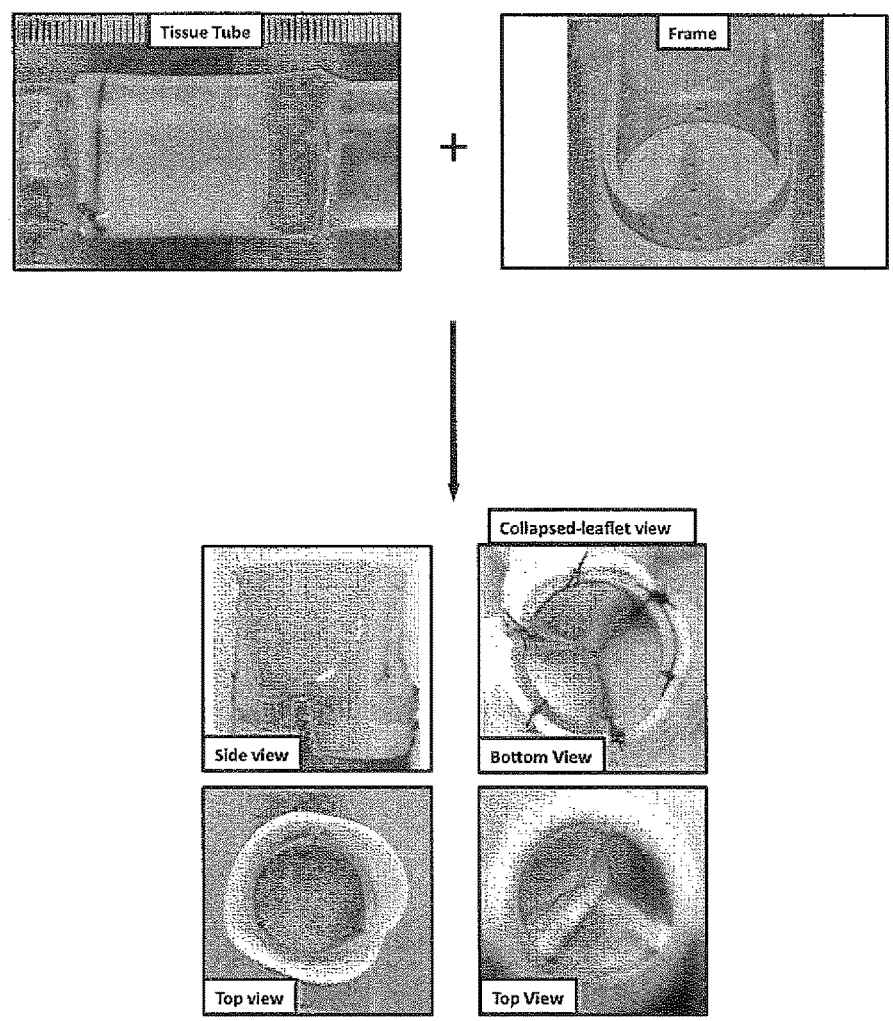

In addition to the embodiment shown in FIG. 2, three points of anchorage can be made using a material that is placed inside (e.g., a stent) or outside (e.g., a frame) the tubular graft, which can be made of a rigid material for a frame (e.g. titanium) or a flexible material for a stent (e.g. braided Nitinol wire mesh). FIG. 3 shows an embodiment in which a tissue tube is placed on the outside of a rigid frame containing three struts as anchoring points.

In addition to the anchoring methods described herein, which can be used to make tissue-engineered valves, methods of modifying the biologically-engineered tubular graft also are provided. For example, a biologically-engineered tubular graft can be formed with controlled release agents, or conjugated with biomolecules, or cross-linked, or recellularized.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Production and Implantation of Tubular Graft

Engineered grafts (4 mm ID, 2-3 cm long, 0.4 mm thickness) were fabricated from ovine dermal fibroblasts using the pulsed-flow-stretch (PFS) bioreactor and decellularized using sequential treatment with SDS, Triton-X, and DNase, which had little effect on graft properties. The total graft culture time was 7 weeks. The burst pressure of the decellularized grafts exceeded 4000 mm Hg and had the same compliance as the ovine femoral artery. No cells were visible with histological staining and DNA content was less than 10% of the untreated grafts. The decellularized grafts were implanted interpositionally in the femoral or carotid artery of 4 sheep (n=6) for 8 weeks, in some cases the contralateral position being used for a graft or sham control, where the native artery segment being sutured back into place, and into 2 sheep (n=4) for 24 weeks. Anticoagulation therapy was used for the duration, but no immunosuppression was used.

Example 2—Physiology of Implanted Tubular Grafts

At both 8 and 24 weeks, all grafts were patent and showed no evidence of dilatation or mineralization. Mid-graft lumen diameter was unchanged. Lumen diameter at the ends was 15% smaller for the grafts at 7 weeks based on echocardiography, with a similar trend for the controls, but this was not statistically significant at 24 weeks. A thin neointima was evident near the ends of the grafts. Extensive recellularization occurred, with most cells expressing SMA. Deposition of organized elastin was evident. Endothelialization was complete at the ends of the grafts and partial mid-graft at 8 weeks and complete at 24 weeks. Complementary in vitro studies with a parallel plate flow chamber also indicate excellent shear resistance at physiological shear stresses of pre-seeded blood outgrowth endothelial cells and mesenchymal stem cells. These studies indicate that the completely biological grafts possessing circumferential alignment/tensile anisotropy, can be implanted into the arterial circulation without dilation or mineralization and minor intimal hyperplasia, and with favorable cell seeding, recellularization, and matrix remodeling.

Example 3—A Tissue-Engineered Tubular Valve

A tissue-engineered tubular graft having a lumen diameter of about 15-30 mm was decellularized as described in Example 1. One end of the tube was anchored at three points spaced approximately equally around the circumference of the tube using a suture (as shown schematically in FIG. 1).

FIG. 3 shows an embodiment in which a tissue tube is anchored around a rigid frame. The tissue tube was sleeved over the outside of the frame and stitched along the three posts and around the bottom rim using a prolene suture. Under fluid back-pressure, the tissue tube collapses between the three posts and creates a valvular action similar to a tri-leaflet valve.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of treating cardiovascular disease comprising implanting a biologically engineered tubular product into a native vessel, wherein the biologically engineered tubular product is formed from cell-produced extracellular matrix cultured under conditions that comprise providing or allowing a fibrin gel composition, as it remodels into the cell-produced extracellular matrix, to axially shorten while circumferentially stretching or distending the fibrin gel composition, thereby producing the biologically engineered tubular product.

2. The method of claim 1, wherein the native vessel is an artery or vein.

3. The method of claim 1, wherein implanting includes replacing.

4. The method of claim 1, wherein implanting includes placing into or replacing a heart valve.

5. The method of claim 1, wherein said fibrin gel composition is formed from matrix-producing cells, fibrinogen, and thrombin.

6. The method of claim 1, wherein said biologically engineered tubular product is decellularized.

7. The method of claim 1, wherein the biologically engineered tubular product further comprises controlled release agents or biomolecules.

8. The method of claim 1, wherein the biologically engineered tubular product is capable of repopulating cells after implantation or engraftment in vivo.

9. The method of claim 1, wherein the biologically engineered tubular product is capable of recellularization after implantation or engraftment in vivo.

10. The method of claim 1, wherein the native vessel is selected from the group consisting of a thoracic aorta, an abdominal aorta, aortic arch vessels, iliac arteries, a femoral artery, and a carotid artery.

11. The method of claim 1, wherein implanting comprises implanting into the arterial circulation.

* * * * *